United States Patent
Teles et al.

[11] Patent Number: 5,808,114
[45] Date of Patent: Sep. 15, 1998

[54] PREPARATION OF EPOXIDES BY MEANS OF AROMATIC PEROXYCARBOXYLIC ACIDS

[75] Inventors: Joaquim Henrique Teles, Ludwigshafen; Werner Schnurr, Herxheim; Rolf Fischer, Heidelberg; Norbert Rieber, Mannheim; Michael Schulz, Ludwigshafen, all of Germany

[73] Assignee: BASF Aktiengesellschaft, Ludwigshafen, Germany

[21] Appl. No.: 875,607

[22] PCT Filed: Feb. 10, 1996

[86] PCT No.: PCT/EP96/00578

§ 371 Date: Aug. 5, 1997

§ 102(e) Date: Aug. 5, 1997

[87] PCT Pub. No.: WO96/26198

PCT Pub. Date: Aug. 29, 1996

[30] Foreign Application Priority Data

Feb. 21, 1995 [DE] Germany .................. 195 05 858.5

[51] Int. Cl.⁶ .................................................. C07D 301/14
[52] U.S. Cl. .............................................................. 549/525
[58] Field of Search ............................................... 549/525

[56] References Cited

U.S. PATENT DOCUMENTS 4,010,195  3/1977  Isogai et al. ............................. 423/587

FOREIGN PATENT DOCUMENTS

| 568337 | 11/1993 | European Pat. Off. . |
| 1440125 | 8/1966 | France . |
| 2312281 | 9/1974 | Germany . |
| 2515033 | 10/1975 | Germany . |
| 44 28 994 | 2/1996 | Germany . |
| WO 96/05161 | 2/1996 | WIPO . |

OTHER PUBLICATIONS

Y. Sawaki, Wiley Interscience, pp. 590–595, 1993, "Supply. E2: The Chemistry of Hydroxyl, Ether and Peroxide Groups".

Primary Examiner—Amelia Owens
Attorney, Agent, or Firm—Oblon, Spivak, McClelland, Maier & Neustadt, P.C.

[57] ABSTRACT

Preparation of epoxides from olefins by means of aromatic peroxycarboxylic acids comprises a step A of epoxidizing the olefin and removing the resulting aromatic carboxylic acid from the epoxide, a step B of catalytically hydrogenating the removed aromatic carboxylic acid to the corresponding aromatic aldehyde, and a step C of oxidizing this aldehyde with oxygen or an oxygen-containing gas mixture back to the aromatic peroxycarboxylic acid for re-use for epoxidizing an olefin.

9 Claims, No Drawings

PREPARATION OF EPOXIDES BY MEANS OF AROMATIC PEROXYCARBOXYLIC ACIDS

BACKGROUND OF THE INVENTION

1. Field of the Invention

The present invention relates to an improved process for preparing epoxides, in particular alkylene oxides, from corresponding starting compounds, in particular from the corresponding olefins, by means of aromatic peroxycarboxylic acids.

2. Description of the Background

The epoxidation of olefins with peroxycarboxylic acids, in particular with m-chloroperoxybenzoic acid, is a well established laboratory method for the synthesis of epoxides.

The method is extensively described in the chemical literature, for example by Y. Sawaki in S. Patai (ed.), Chem. Hydroxyl, Ether Peroxide Groups, p. 590–593 (1993) (1).

However, the method is less suitable for preparing epoxides on a larger scale, since the peroxycarboxylic acid is used in stoichiometric amounts and the resulting carboxylic acid has to be expensively regenerated by reaction with hydrogen peroxide.

SUMMARY OF THE INVENTION

It is an object of the present invention to provide a process for preparing alkylene oxides by epoxidation of olefins with aromatic peroxycarboxylic acids which permits a simple, safe and economical recycle of the resulting carboxylic acid into peroxycarboxylic acid without use of hydrogen peroxide.

We have found that this object is achieved by a process for preparing an epoxide from the corresponding olefin by means of an aromatic peroxycarboxylic acid, which comprises a step A of epoxidizing the olefin and removing the resulting aromatic carboxylic acid from the epoxide, a step B of catalytically hydrogenating the removed aromatic carboxylic acid to the corresponding aromatic aldehyde, and a step C of oxidizing this aldehyde with oxygen or an oxygen-containing gas mixture back to the aromatic peroxycarboxylic acid for re-use for preparing an epoxide.

DETAILED DESCRIPTION OF THE INVENTION

In principle, any olefin can be epoxidized in step A. Preference is given to olefins which carry not more than one electron-attracting substituent directly on the double bond. Particular preference is given to olefins without electron-attracting substituents on the double bond. Examples of useful olefins are linear or branched $C_2$–$C_{40}$-olefins, in particular $C_3$–$C_{24}$-olefins, or cyclic olefins, such as ethylene, propene, 1-butene, 2-butene, isobutene, 1-pentene, 2-pentene, 1-hexene, 1-heptene, 1-octene, 2,4,4-trimethyl-1-pentene, 2,4,4-trimethyl-2-pentene, 1-nonene, 1-decene, 1-dodecene, 1-tetradecene, 1-hexadecene, 1-octadecene, $C_{20}$-olefin, $C_{22}$-olefin, $C_{24}$-olefin, $C_{28}$-olefin or $C_{30}$-olefin, cyclopropene, cyclobutene, cyclopentene, cyclohexene, cyclooctene, vinyl alkyl ethers such as vinyl methyl ether, vinyl ethyl ether or vinyl butyl ether, allyl chloride, allyl alcohol, vinyl acetate, vinyl propionate, styrene and also compounds having a plurality of olefinic double bonds such as 1,3-butadiene, isoprene, cyclopentadiene or cyclooctadiene. It is also possible to use olefin mixtures.

The process of the present invention is particularly highly suitable for epoxidizing propene to propylene oxide.

Suitable aromatic peroxycarboxylic acids are in particular compounds of the general formula I

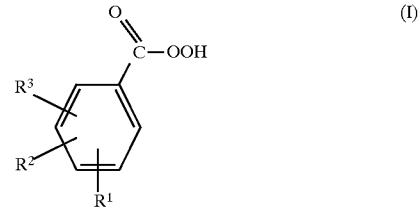

where $R^1$ to $R^3$ are independently of one another hydrogen, $C_1$–$C_6$-alkyl, $C_3$–$C_8$-cycloalkyl, $C_6$–$C_{14}$-aryl, $C_7$–$C_{12}$-phenylalkyl, halogen, $C_1$–$C_6$-alkoxy, $C_3$–$C_8$-cycloalkoxy, $C_6$–$C_{14}$-aryloxy or $C_7$–$C_{12}$-phenylalkoxy and one of $R^1$ to $R^3$ can also be a further peroxycarboxyl group or a carboxyl group.

More particularly, the substituents $R^1$ to $R^3$ have independently the following meanings:

hydrogen;
$C_1$–$C_6$-alkyl, preferably $C_1$–$C_4$-alkyl such as methyl, ethyl, n-propyl, isopropyl, n-butyl, isobutyl, sec-butyl, tert-butyl, n-pentyl or n-hexyl, in particular methyl or tert-butyl;
$C_3$–$C_8$-cycloalkyl such as cyclopropyl, cyclobutyl, cyclopentyl, cyclohexyl, cycloheptyl or cyclooctyl, in particular cyclopentyl or cyclohexyl or substituted $C_3$–$C_8$-cycloalkyl, in particular 1-methylcyclopentyl or 1-methylcyclohexyl;
$C_6$–$C_{14}$-aryl such as phenyl, 1-naphthyl, 2-naphthyl, 1-anthryl, 2-anthryl or 9-anthryl, in particular phenyl;
$C_7$–$C_{12}$-phenylalkyl such as 1-methyl-1-phenylethyl, benzyl, 1-phenylethyl, 2-phenylethyl, 1-phenylpropyl, 2-phenylpropyl, 3-phenylpropyl, 1-phenylbutyl, 2-phenylbutyl, 3-phenylbutyl or 4-phenylbutyl, in particular 1-methyl-1-phenylethyl;
halogen such as fluorine, chlorine or bromine;
$C_1$–$C_6$-alkoxy, $C_3$–$C_8$-cycloalkoxy, $C_6$–$C_{14}$-aryloxy or $C_7$–$C_{12}$-phenylalkoxy, in which case the radicals on the oxygen atom have the above-innumerated meanings of $R^1$ to $R^3$ (with the exception of hydrogen);
peroxycarboxyl or carboxyl for one of $R^1$ to $R^3$.

Preference is further given to those aromatic peroxycarboxylic acids I which have one, two or three methyl groups as substituents $R^1$ to $R^3$.

Examples of useful aromatic peroxycarboxylic acids are in particular peroxybenzoic acid, 2-methylperoxybenzoic acid (o-peroxytoluic acid), 3-methylperoxybenzoic acid (m-peroxytoluic acid), 4-methylperoxybenzoic acid (p-peroxytoluic acid), 2,4- and 3,5-dimethylperoxybenzoic acid, 2,4,6-trimethylperoxybenzoic acid, 4-tert-butylperoxybenzoic acid, 2-methyl-4-tert-butylperoxybenzoic acid, 2,6-dimethyl-4-tert-butylperoxybenzoic acid, 2-, 3- or 4-ethylperoxybenzoic acid, 4-(1-methylcyclohexyl)peroxybenzoic acid, 4-(1-methylcyclopentyl)peroxybenzoic acid, 4-phenylperoxybenzoic acid, 3-chloroperoxybenzoic acid, 4-methoxy- or 4-ethoxy-peroxybenzoic acid, 4-methoxy- or 4-ethoxy-2,6-dimethylperoxybenzoic acid, bisperoxyphthalic acid, monoperoxyphthalic acid, bisperoxyterephthalic acid and monoperoxyterephthalic acid. It is also possible to use mixtures of the aromatic peroxycarboxylic acids mentioned. o-Peroxytoluic acid is particularly preferred.

Step A of the process of the present invention is described in the literature as regards the epoxidation of olefins. The epoxidation is typically carried out as follows:

The aromatic peroxycarboxylic acid, dissolved in a suitable solvent, is made to react with an olefin. The molar ratio of olefin to peroxycarboxylic acid is within the range from 0.8:1 to 100:1, in particular from 1:1 to 20:1, especially from 1.5:1 to 5:1.

The peroxycarboxylic acid solution used can be an isolated peroxycarboxylic acid dissolved in a solvent. It is preferable, however, to use directly the solution prepared in oxidation step C (with or without a prior purification step during which the peroxycarboxylic acid remains in solution).

Suitable organic solvents for the peroxycarboxylic acids in the epoxidation are ketones (e.g., acetone, butanone or tert-butyl methyl ketone), esters (e.g., methyl or ethyl acetate or methyl benzoate), nitro compounds (e.g., nitromethane or nitrobenzene), halogenated hydrocarbons (e.g., di- or trichloromethane, 1,1,1-trichloroethane or chlorobenzene), carbonates (e.g., dimethyl carbonate), urea derivatives (e.g., tetramethylurea), inorganic esters or amides (e.g., trimethyl phosphate or hexamethylphosphoramide), hydrocarbons (e.g., hexane or heptane), or alkylaromatics (e.g., benzene, toluene or xylene). However, it is particularly preferable to use the same solvent as in the oxidation of step C. Particularly preferred solvents for both steps are acetone, methyl acetate and ethyl acetate.

The epoxidation can be carried out at from −20° to 100° C., depending on solvent and olefin. If acetone is used as solvent and terminal olefins (e.g., 1-octene or propene) as substrate, temperatures from 25° to 80° C. are preferred. Temperatures from 45° to 65° C. are particularly preferred.

Surprisingly, at the relatively high temperature of 45° C. or higher, the olefin is converted much more rapidly to the epoxide than any aromatic aldehyde still present from stage B is converted to carboxylic acid.

The aromatic carboxylic acids formed in step A from the aromatic peroxycarboxylic acids I are separated from the oxidation products, in particular the alkylene oxides, by customary methods, for example by filtration, extraction or distillation.

The catalytic hydrogenation of the aromatic carboxylic acids in step B is preferably effected with hydrogen in the gas phase in the presence of a lanthanide/zirconia catalyst. Such catalysts are known for use as hydrogenation catalysts for converting aromatic carboxylic acids into the corresponding aldehydes from German Patent Application P 44 28 994.4 (2).

Step B of the process of the present invention is advantageously carried out as follows:

The hydrogenation of the aromatic carboxylic acid with hydrogen is carried out in the presence of a catalyst whose catalytically active material comprises from 60 to 99.9, in particular from 80 to 99.9, % by weight of zirconium oxide ($ZrO_2$) and from 0.1 to 40, in particular from 0.1 to 20, % by weight of one or more elements of the lanthanides, is generally carried out at temperatures from 200° to 450° C., preferably from 250° to 400° C., in particular from 300° to 380° C., and pressures from 0.1 to 20 bar, preferably from 0.7 to 5 bar, in particular at atmospheric pressure. The temperature and pressure required are dependent on the catalyst activity and the thermal stability of precursor and product.

Suitable catalysts include supported catalysts, preferably solid catalysts of zirconium oxide in cubic, tetragonal or monoclinic phase, preferably in monoclinic phase, which have been doped with one or more elements of the lanthanide series. The catalytically active mass comprises preferably from 90 to 99.9% by weight, in particular from 92 to 99% by weight, of zirconium oxide and from 0.1 to 10% by weight, in particular from 1 to 8% by weight, of one or more elements of the lanthanides, in particular lanthanum, cerium, praseodymium, neodymium, samarium, europium or mixtures thereof, especially lanthanum as lanthanum(III) oxide. The doping is generally effected by saturating the zirconium oxide with salt solutions (aqueous or alcoholic) of the lanthanides.

The catalyst may additionally include further dopants (e.g., chromium, iron, yttrium, hafnium, manganese) in amounts from 0.001 to 10% by weight. Preference is given to catalysts without such further additions.

The BET surface area of the zirconium oxide can vary within wide limits and is generally from 5 to 150 $m^2/g$, preferably from 20 to 150 $m^2/g$, in particular from 40 to 120 $m^2/g$.

Catalysts of this type are produced in a conventional manner, for example by saturating preformed carrier elements such as pellets, balls or extrudates, drying and calcining.

The preferred supported catalysts are very active over a prolonged period. Deactivated catalysts can be regenerated by treatment with gases containing molecular oxygen, e.g., air, at temperatures from 350° to 500° C.

The weight hourly space velocity over the catalyst is held in general within the range from 0.01 to 10, preferably from 0.01 to 3, kg of aromatic carboxylic acid per kg of catalyst per hour.

The hydrogen concentration in the feed gas depends on the carboxylic acid concentration. The molar ratio of hydrogen to aromatic carboxylic acid is in general within the range from 2:1 to 100:1, preferably within the range from 10:1 to 70:1. The hydrogen can also come from formic acid used as source.

It can also be advantageous to add an inert diluent. Typically, nitrogen, water or gaseous reaction-inert compounds such as hydrocarbons, aromatics or ethers are employed.

The reaction can be carried out in the gas phase, continuously as a fixed bed reaction with a fixed bed catalyst, for example in an upflow or downflow process, or as a fluidized bed reaction with the catalyst in the fluidized state. Preference is given to the use of a fixed bed.

To increase the selectivity, by-products of the hydrogenation, for example alcohols, can be recycled into the synthesis.

The step B exit mixture, containing the aromatic aldehyde, passes with or without prior purification into step C where it is advantageously taken up in a suitable solvent and oxidized in the liquid phase with oxygen or an oxygen-containing gas mixture to the corresponding aromatic percarboxylic acid. This is preferably done at temperatures from −10° C. to 100° C. and oxygen partial pressures from 0.001 to 100 bar.

DE-A-25 15 033 (3) discloses that p-tolualdehyde can be oxidized in acetone solution with air at 28° C. and 30 bar without catalyst to form p-peroxytoluic acid in a yield of about 80%. However, such high yields are only achieved with highly pure p-tolualdehyde and anhydrous acetone.

Step C of the process of the present invention is normally carried out as follows:

The concentration of the aromatic aldehyde in the solvent can be from 1 to 75% by weight. Preferably it is from 5 to 35% by weight, in particular from 8 to 20% by weight.

Oxygen or the oxygen-containing gas mixture can be made to react with the aromatic aldehyde either in gas form or as a solution, under atmospheric or superatmospheric pressure. The oxygen partial pressure is preferably from 0.01 to 30 bar, in particular from 0.05 to 5 bar.

The oxidation can be carried out mono- or diphasicly. Suitable reactors for the monophasic process are ones in which a solution of the aromatic aldehyde can be reacted with a solution of oxygen, under atmospheric or superatmospheric pressure, for example tubular reactors or flooded stirred tanks. Suitable reactors for the diphasic process ensure thorough gas-liquid mixing, such as bubble columns (with or without dividing walls or packing elements), stirred tanks (optionally equipped with sparging agitators and optionally arranged as a cascade) or trickle downflow reactors.

The reaction temperature is preferably from 0° to 60° C., in particular from 15° to 40° C.

The reaction time is chosen so as to produce an aldehyde conversion within the range from 40 to 100%. Preference is given to reaction times producing an aldehyde conversion within the range from 60 to 99%. Particular preference is given to reaction times producing an aldehyde conversion within the range from 75 to 95%.

The oxidation may additionally comprise a step of adding a stabilizer for the peroxycarboxylic acid product, e.g., 8-hydroxyquinoline, dipicolinic acid or 2,6-dihydroxymethylpyridine.

Suitable organic solvents for step C are ketones (e.g., acetone, butanone or tert-butyl methyl ketone), esters (e.g., methyl or ethyl acetate or methyl benzoate), nitro compounds (e.g., nitromethane or nitrobenzene), halogenated hydrocarbons (e.g., di- or trichloromethane, 1,1,1-trichloroethane or chlorobenzene), carbonates (e.g., dimethyl carbonate), urea derivatives (e.g., tetramethylurea), inorganic esters or amides (e.g., trimethyl phosphate or hexamethylphosphoramide) or alkylaromatics (e.g., benzene, toluene or xylene). Preference is given to ketones, in particular acetone and tert-butyl methyl ketone, and esters, in particular methyl acetate, ethyl acetate and methyl benzoate.

The aromatic peroxycarboxylic acid can either by isolated (by precipitation, for example), or else be re-used directly in step A without isolation (i.e., in solution).

It is surprising that o-tolualdehyde is faster and more selectively oxidizable than the isomeric m- and p-tolualdehydes.

The process of the present invention has the advantage that the aromatic peroxycarboxylic acid is regenerated without use of hydrogen peroxide after the oxidation/epoxidation. The aromatic peroxycarboxylic acid acts only as an oxygen transfer agent and is not consumed to any practical extent. The stoichiometry of the overall process is:

$$\text{olefin} + O_2 + H_2 \rightarrow \text{alkylene oxide} + H_2O.$$

A reaction scheme for the epoxidation using an aromatic peroxycarboxylic acid I may be illustrated as follows:

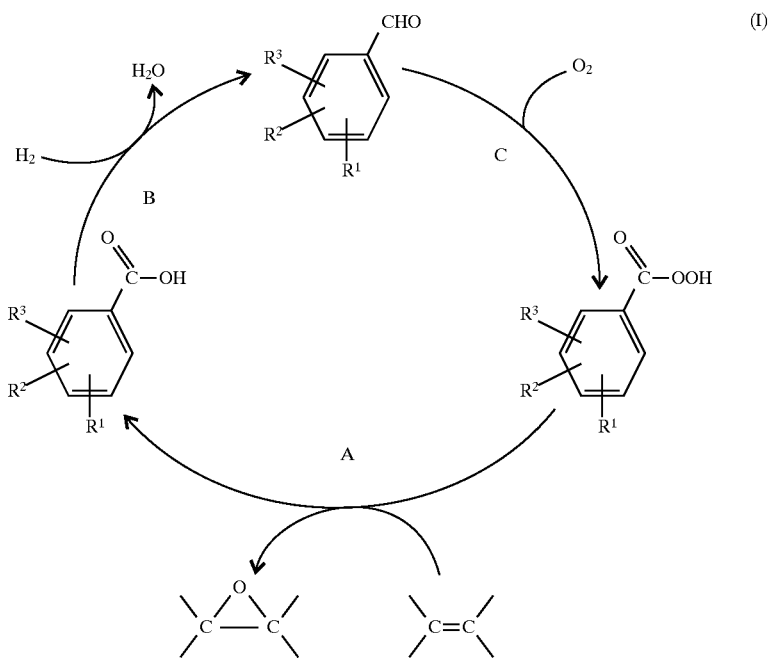

EXAMPLES

Example 1

Epoxidation of 1-octene with p-peroxytoluic Acid in Acetone 50 g of an 8.3% strength by weight solution of p-peroxytoluic acid in acetone were admixed with 4.6 g (1.5 equivalents) of 1-octene and stirred at 40° C. for 5 hours, when the conversion of the peroxyacid was about 90%. The octene oxide selectivity was about 80%, based on the peroxyacid, and >95%, based on 1-octene. The reaction temperature was raisable without significantly reducing the selectivity. At a reaction temperature of 60° C. the peroxyacid conversion after 2 hours was about 90%. The octene oxide selectivity was unchanged compared with the run at 40° C.

Example 2

Epoxidation of Propene with p-peroxytoluic Acid in Acetone 35 g of an 8.4% strength by weight solution of p-peroxytoluic acid in acetone were charged initially to a 50 ml glass autoclave, 2.4 g of propene (3 equivalents) were injected, and the contents were stirred at 60° C. for 4.5 hours. The peroxyacid conversion was 94%. The propylene oxide selectivity based on the peroxyacid was >95%.

Example 3

Epoxidation of 1-octene with o-peroxytoluic Acid in Acetone 100 g of an 11.3% strength by weight solution of o-peroxytoluic acid in acetone were admixed with 16.8 g of 1-octene (2 equivalents) and stirred at 60° C. After 1 hour the peroxyacid conversion was 92%. The octene oxide selectivity was 97%, based on o-peroxytoluic acid.

were passed into a vaporizer (<300° C.) and carried from there by 100 l/h of hydrogen through 100 g of catalyst in a trickle downflow. The gaseous reaction effluent was condensed in cold traps and analyzed by gas chromatography. The carboxylic acids used and the results are summarized in Table 1.

TABLE 1

| Ex. No. | Catalyst | Carboxylic acid R[1)] | Conc. of carboxylic acid [wt. %][2)] | Reactor temp. [°C.] | Yield of aldehyde [%] | Conversion [%] | Selectivity [%] |
|---|---|---|---|---|---|---|---|
| 5a | A | H | 100 | 340 | 98 | 100 | 98 |
| 5b | A | H | 20 | 350 | 98 | 100 | 98 |
| 5c | A | methyl | 100 | 340 | 96 | 99 | 97 |
| 5d | A | t-butyl | 100 | 340 | 90 | 94 | 96 |
| 5e | A | t-butyl | 20 | 340 | 93 | 97 | 96 |
| 5f | A | methyl | 10 | 350 | 77 | 99 | 78 |
| 5g | B | H | 100 | 360 | 95 | 100 | 95 |
| 5h | C | H | 100 | 360 | 96 | 100 | 96 |
| 5i | D | H | 100 | 360 | 97 | 99 | 98 |

[1)]substituent in position 4 of the carboxylic acid: 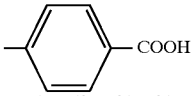

[2)]in solvent (THF); 100% by weight indicates pure carboxylic acid, without solvent Example 4

Preparation of the Catalyst for the Hydrogenation in Step B

Monoclinic $ZrO_2$ (BET surface area: 40–85 $m^2/g$) in the form of tablets (catalysts A and E) or extrudates (catalysts B, C and D) was saturated with an aqueous solution of the lanthanide element nitrate (or lanthanide element nitrates) by thorough mixing and the mixture was held at room temperature for 2 hours. The catalyst was then dried at 120° C. for 15 hours and then heat-treated at from 400° to 500° C. for from 2 to 4 hours.

The catalysts thus prepared had the following lanthanide contents:

Catalyst A (surface area: 67 $m^2/g$): 3% by weight of lanthanum;
Catalyst B (surface area: 46 $m^2/g$): 3% by weight of praseodymium;
Catalyst C (surface area: 46 $m^2/g$): 3% by weight of cerium;
Catalyst D (surface area: 46 $m^2/g$): 3% by weight of lanthanides (distribution: 48.2% by weight of $CeO_2$, 26.4% by weight of $La_2O_3$, 5.7% by weight of $Pr_2O_3$ and 19.7% by weight of $Nd_2O_3$);
Catalyst E (surface area: 53 $m^2/g$): 3% by weight of lanthanum.

Examples 5a to 5i

Hydrogenation of 4-substituted Aromatic Carboxylic Acids

Per hour, from 4 to 8 g of aromatic carboxylic acid, without a solvent or dissolved in tetrahydrofuran (THF), Example 6

Hydrogenation of 3-methylbenzoic Acid

Hydrogen at 100 l/h was used to vaporize 8 g/h of 3-methylbenzoic acid (as melt) and pass it at 360° C. in the downflow direction through 100 g of catalyst E. The gaseous reaction effluent was condensed in cold traps and analyzed by gas chromatography. The yield of 3-methylbenzaldehyde was 92% (conversion 99%).

Example 7

Hydrogenation of 2-methylbenzoic Acid

Hydrogen at 200 l/h was used to vaporize 8 g/h of 2-methylbenzoic acid (as melt) and pass it at 350° C. in the downflow direction through 100 g of catalyst E. The gaseous reaction effluent was condensed in cold traps and analyzed by gas chromatography. The yield of 2-methylbenzaldehyde was 93% (conversion 99%).

Examples 8a to 8e

Oxidation of Aromatic Aldehydes with Air to Peroxycarboxylic Acids in Acetone

A solution of aromatic aldehyde (10% strength by weight in acetone) was oxidized with air at 30° C. in a four-neck flask equipped with gas inlet tube, high-speed Hoesch stirrer, a thermometer and a reflux condenser. The peroxyacid concentration was determined by iodometry. Other components can be determined by gas chromatography (after reduction of the peroxyacid with tributyl phosphite). The aldehydes used and the results are summarized in Table 2.

TABLE 2

| Ex. No. | Aldehyde | Reaction time [h] | Conversion of aldehyde [%] | Peroxyacid selectivity [%] |
|---|---|---|---|---|
| 8a | benzaldehyde | 2 | 34 | 77 |
| 8b | p-tolualdehyde | 7 | 84 | 83 |
| 8c | m-tolualdehyde | 6 | 90 | 82 |
| 8d | o-tolualdehyde | 4 | 80 | 93 |
| 8e | p-methoxy-benzaldehyde | 1 | 37 | 72 |

Example 9

Oxidation of p-tolualdehyde in Methyl Acetate

Example 8b was repeated with methyl acetate instead of acetone as solvent. After 7 hours of reaction the aldehyde conversion was 62%. The p-peroxytoluic acid selectivity was 69%.

Example 10

Oxidation of o-tolualdehyde with Oxygen under Superatmospheric Pressure

A 10% strength by weight solution of o-tolualdehyde in acetone was oxidized at 5 bar and 30° C. with pure oxygen in a magnetically stirred 10 ml glass autoclave. After 1.5 hours the aldehyde conversion was about 80%. o-Peroxytoluic acid had been formed with a selectivity of >90%. The rest was chiefly o-toluic acid. By-products such as phthalide, toluene, o-cresol and o-cresol formate were formed with a selectivity of only about 0.2%.

The oxidation could also be carried out in more concentrated solutions. The oxidation of a 20% strength by weight solution of o-tolualdehyde (30° C., 5 bar oxygen, 3 hours reaction time) yielded the corresponding peroxyacid with a selectivity of about 93% (aldehyde conversion: 90%).

We claim:

1. A process for preparing an alkylene oxide from the corresponding olefin by means of an aromatic peroxycarboxylic acid, which comprises a step A of epoxidizing the olefin and removing the resulting aromatic carboxylic acid from the alkylene oxide, a step B of catalytically hydrogenating the removed aromatic carboxylic acid to the corresponding aromatic aldehyde, and a step C of oxidizing this aldehyde with oxygen or an oxygen-containing gas mixture back to the aromatic peroxycarboxylic acid for re-use for epoxidizing an olefin.

2. A process as claimed in claim 1 wherein propene is epoxidized to propylene oxide.

3. A process as claimed in claim 1 wherein the aromatic peroxycarboxylic acid used is a compound of the general formula I

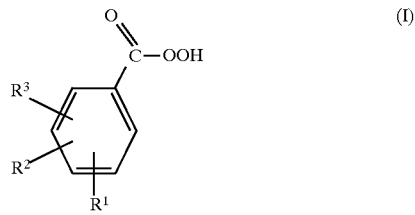

where $R^1$ to $R^3$ are independently of one another hydrogen, $C_1-C_6$-alkyl, $C_3-C_8$-cycloalkyl, $C_6-C_{14}$-aryl, $C_7-C_{12}$-phenylalkyl, halogen, $C_1-C_6$-alkoxy, $C_3-C_8$-cycloalkoxy, $C_6-C_{14}$-aryloxy or $C_7-C_{12}$-phenylalkoxy and one of $R^1$ to $R^3$ can also be a further peroxycarboxyl group or a carboxyl group.

4. A process as claimed in claim 1 wherein the step B catalytic hydrogenation of the aromatic carboxylic acid is carried out with hydrogen in the gas phase in the presence of a lanthanide/zirconia catalyst.

5. A process as claimed in claim 1 wherein the step C oxidation of the aromatic aldehyde is carried out in the liquid phase in a suitable solvent at temperatures from −10° C. to 100° C. and oxygen partial pressures from 0.001 to 100 bar.

6. A process as claimed in claim 1 wherein the epoxidation is carried out in a solvent.

7. A process as claimed in claim 1 wherein the epoxidation and the oxidation of the aldehyde are carried out in the same solvent.

8. A process as claimed in claim 7 wherein the solvent used is acetone, methyl acetate or ethyl acetate.

9. A process as claimed in claim 3 wherein the peroxycarboxylic acid used is o-peroxytoluic acid.

* * * * *